(12) United States Patent
Slutzky et al.

(10) Patent No.: US 10,175,755 B2
(45) Date of Patent: Jan. 8, 2019

(54) DEVICE AND METHOD FOR TREATING ABNORMAL MUSCLE FUNCTION

(71) Applicant: Northwestern University, Evanston, IL (US)

(72) Inventors: Marc W. Slutzky, Northbrook, IL (US); Zachary A. Wright, Orland Park, IL (US); Eric W. Lindberg, Chicago, IL (US)

(73) Assignee: Northwestern University, Evanston, IL (US)

( * ) Notice: Subject to any disclaimer, the term of this patent is extended or adjusted under 35 U.S.C. 154(b) by 710 days.

(21) Appl. No.: 14/469,727

(22) Filed: Aug. 27, 2014

(65) Prior Publication Data

US 2015/0064662 A1    Mar. 5, 2015

Related U.S. Application Data

(60) Provisional application No. 61/870,445, filed on Aug. 27, 2013.

(51) Int. Cl.
| | |
|---|---|
| *G06F 3/01* | (2006.01) |
| *A61B 5/0488* | (2006.01) |
| *G09B 19/00* | (2006.01) |
| *G09B 5/00* | (2006.01) |
| *A61B 5/00* | (2006.01) |

(52) U.S. Cl.
CPC ............ *G06F 3/015* (2013.01); *A61B 5/0488* (2013.01); *A61B 5/486* (2013.01); *G09B 5/00* (2013.01); *G09B 19/003* (2013.01); *G09B 19/0053* (2013.01)

(58) Field of Classification Search
CPC ....... G06F 3/015; A61B 5/0488; A61B 5/486; G09B 5/00; G09B 19/003; G09B 19/0053
USPC .......................................................... 434/118
See application file for complete search history.

(56) References Cited

U.S. PATENT DOCUMENTS

| | | | |
|---|---|---|---|
| 7,252,644 B2 | 8/2007 | Dewald et al. | |
| 2007/0066918 A1 | 3/2007 | Dewald et al. | |
| 2009/0005700 A1* | 1/2009 | Joshi | A61B 5/0488 600/546 |
| 2011/0137196 A1* | 6/2011 | Kakei | A61B 5/0488 600/546 |

OTHER PUBLICATIONS

Beer RF, Dewald JP, Rymer WZ. "Deficits in the coordination of multijoint arm movements in patients with hemiparesis: evidence for disturbed control of limb dynamics," Exp Brain Res. 2000;131(3):305-319.

(Continued)

*Primary Examiner* — Robert P Bullington
(74) *Attorney, Agent, or Firm* — Cook Alex Ltd.

(57) ABSTRACT

A myoelectric computer interface device is disclosed that includes a myoelectric controller, a computer interface and a monitor. The computer interface includes at least one computer-implementable software program that comprises executable code, wherein the executable code comprises at least one member selected from the group consisting of: instructions for mapping at least one muscle activity to cursor icon movement and instructions for orthogonal or other mapping of co-activated muscles.

17 Claims, 27 Drawing Sheets

(56) References Cited

OTHER PUBLICATIONS

Chae J, Yang G, Park BK, Labatia L "Muscle weakness and cocontraction in upper limb hemiparesis: relationship to motor impairment and physical disability" Neurorehabil Neural Repair. Sep. 2002;16(3):241-248.

Dewald J, Pope PS, Given JD, Buchanan TS, Rymer WZ. "Abnormal muscle coactivation patterns during isometric torque generation at the elbow and shoulder in hemiparetic subjects," Brain. 1995;118(2):495.

Dewald J, Beer RF. "Abnormal joint torque patterns in the paretic upper limb of subjects with hemiparesis," Muscle & nerve. 2001;24(2):273-283.

Ellis MD, Holubar BG, Acosta AM, Beer RF, Dewald JPA. "Modifiability of abnormal isometric elbow and shoulder joint torque coupling after stroke," Muscle & nerve. 2005;32(2):170-178.

Kwakkel G, Kollen BJ, van der Grand J, Prevo AJH. "Probability of regaining dexterity in the flaccid upper limb," Stroke. 2003;34(9):2181-2186.

Twitchell TE. "The restoration of motor function following hemiplegia in man," Brain. Dec. 1951;74(4):443-480.

Zackowski KM, Dromerick AW, Sahrmann SA, Thach WT, Bastian AJ. "How do strength, sensation, spasticity and joint individuation relate to the reaching deficits of people with chronic hemiparesis?" Brain. May 2004;127(Pt 5):1035-1046.

Brunnström S., Movement Therapy in Hemiplegia: A Neurophysiological Approach, 1970.

\* cited by examiner

1

DEVICE AND METHOD FOR TREATING ABNORMAL MUSCLE FUNCTION

CROSS-REFERENCE TO RELATED APPLICATIONS

This application claims benefit of priority under 35 U.S.C. 119 to U.S. provisional patent application Ser. No. 61/870,445 filed Aug. 27, 2013, and entitled "DEVICE AND METHOD FOR TREATING ABNORMAL MUSCLE FUNCTION," the contents of which are herein incorporated by reference in its entirety.

BACKGROUND

1. Technical Field

The present disclosure relates to myoelectric computer interface devices and their use for retraining muscle functions.

2. Description of Related Art

More than 3.2 million people in the U.S. suffer chronically-impaired upper limb function due to a stroke and other neurologic disorders, such as M S or spinal cord injury. See Kwakkel G, Kollen B J, van der Grond J, Prevo A J H. "Probability of regaining dexterity in the flaccid upper limb," *Stroke*. 2003; 34(9):2181-2186. Impairment of voluntary arm movement can be due not only to weakness and loss of sensation, but also to abnormal co-activation. See Dewald J, Pope P S, Given J D, Buchanan T S, Rymer W Z. "Abnormal muscle coactivation patterns during isometric torque generation at the elbow and shoulder in hemiparetic subjects," *Brain*. 1995; 118(2):495; Beer R F, Dewald J P, Rymer W Z. "Deficits in the coordination of multijoint arm movements in patients with hemiparesis: evidence for disturbed control of limb dynamics," *Exp Brain Res*. 2000; 131(3):305-319; Dewald J, Beer R F. "Abnormal joint torque patterns in the paretic upper limb of subjects with hemiparesis," *Muscle & nerve*. 2001; 24(2):273-283; Zackowski K M, Dromerick A W, Sahrmann S A, Thach W T, Bastian A T. "How do strength, sensation, spasticity and joint individuation relate to the reaching deficits of people with chronic hemiparesis?" *Brain*. May 2004; 127(Pt 5):1035-1046. In contrast to spasticity, which is increased tone during externally-imposed limb movement, abnormal co-activation, sometimes called "abnormal muscle synergy," consists of increased tone during active or attempted voluntary movement by the patient. See Twitchell T E. "The restoration of motor function following hemiplegia in man," *Brain*. December 1951; 74(4):443-480; Brunnstrom S. *Movement therapy in hemiplegia: a neurophysiological approach*: Facts and Comparisons; 1970. For example, stroke survivors often experience co-activation of anterior deltoid with biceps (flexor synergy), and posterior deltoid with triceps (extensor synergy). This constrains their movement to stereotypical patterns. See Twitchell, supra. By reducing abnormal co-activation and restoring more normal patterns of activation, it may be possible to improve function.

Evidence strongly suggests that the amount of impairment caused by co-activation is significant. See Chae J, Yang G, Park B K, Labatia I. "Muscle weakness and cocontraction in upper limb hemiparesis: relationship to motor impairment and physical disability" *Neurorehabil Neural Repair*. September 2002; 16(3):241-248. Moreover, the clearest way to determine the amount of significance is to prospectively treat the co-activation and assess the effects on movement. See Chae et al. supra. Abnormal co-activation can also be defined as abnormal coupling between joint torques. See Beer et al. supra. Ellis et al recently demonstrated that abnormal arm joint torque couplings in stroke survivors could be reduced by training the subjects to isolate individual joint torques with the use of visual feedback. See Ellis M D, Holubar B G, Acosta A M, Beer R F, Dewald J P A. "Modifiability of abnormal isometric elbow and shoulder joint torque coupling after stroke," *Muscle & nerve*. 2005; 32(2):170-178. This intervention also led to an increase in strength, demonstrating the significant role of co-activation in impaired function.

However, this paradigm is not suitable for widespread use outside the clinic, due to the size and expense of the necessary robotic equipment. Thus, there is a need in the art for a more cost-effective and compact means for providing treatment of post-stroke abnormal muscle function.

SUMMARY

In a first respect, a myoelectric computer interface device is disclosed that includes a myoelectric controller, a computer interface and a monitor. The computer interface includes at least one computer-implementable software program that comprises executable code, wherein the executable code comprises at least one member selected from the group consisting of: instructions for mapping at least one muscle activity to cursor icon movement and instructions for orthogonal or other mapping of two or more co-activated muscles.

In a second respect, a method of training the uncoupling of co-activated muscles for a subject is disclosed. The method includes two steps. The first step is providing a myoelectric computer interface device that includes a myoelectric controller, a computer interface and a monitor. The computer interface includes at least one computer-implementable software program that comprises executable code, wherein the executable code comprises at least one member selected from the group consisting of instructions for mapping at least one muscle activity to cursor icon movement and instructions for orthogonal or other mapping of two or more co-activated muscles. The second step is performing at least one task with the subject.

DETAILED DESCRIPTION

A myoelectric-computer interface (MCI) device and method are disclosed that enable healthy subjects to decouple two normally co-activating muscles and stroke subjects to decouple two abnormally co-activating muscles. Moreover, the MCI device and method enabled the majority of stroke subjects to display both subjective and objective evidence of reduced arm impairment. The MCI device and method provide a novel therapeutic approach to directly retrain muscle activation patterns and improve overall arm function in chronic stroke subjects.

MCI Device and Software

Figure 1:
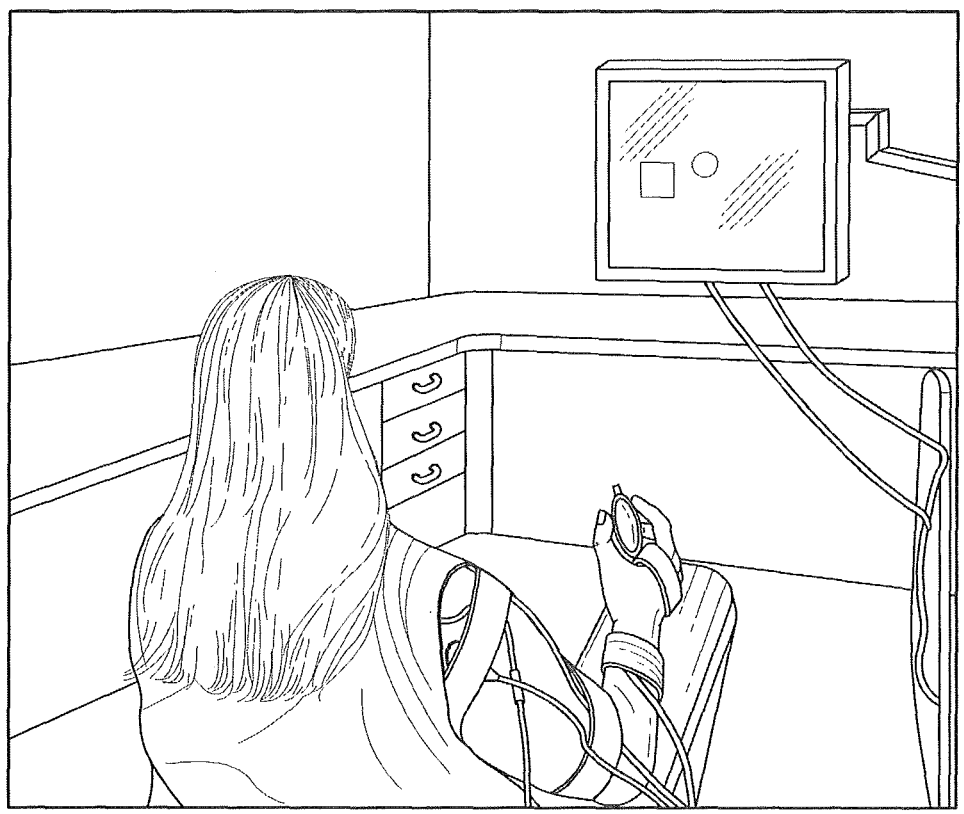
FIG. 1 depicts one embodiment of an experimental setup with one of the stroke subjects, wherein a computer monitor positioned in front of the subject that displays a cursor icon and one or more target icons, wherein the computer monitor is in communication with a computer interface and a myoelectric controller, the latter of which is attached to one or more muscles of the subject.
Figure 2A:
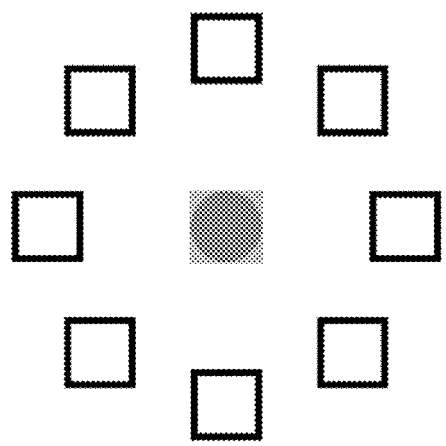
FIG. 2A depicts an embodiment of a schematic of the device task setup in which the subjects view and hold the initial position of the cursor at a center position surrounded by one of either 2 or 8 (shown here) outer targets.
Figure 2B:
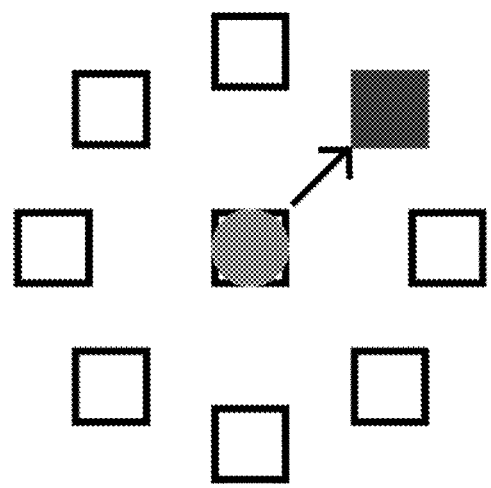
FIG. 2B depicts the embodiment of FIG. 2A, wherein subjects attempted to move the cursor from the center position to one of either 2 or 8 (shown here) outer targets using control signals derived from electromyogram (EGM) activity.
Figure 2C:
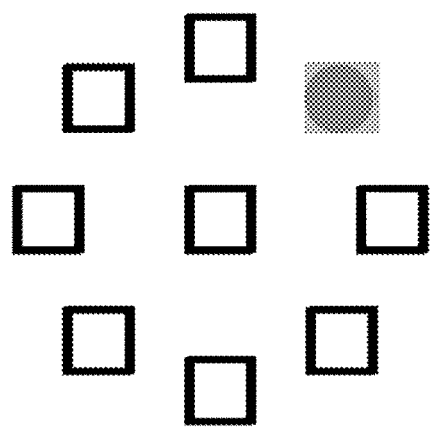
FIG. 2C depicts the embodiment of FIG. 2B, wherein subjects view and hold the final position of the cursor at an outer target following movement.
Figure 2D:
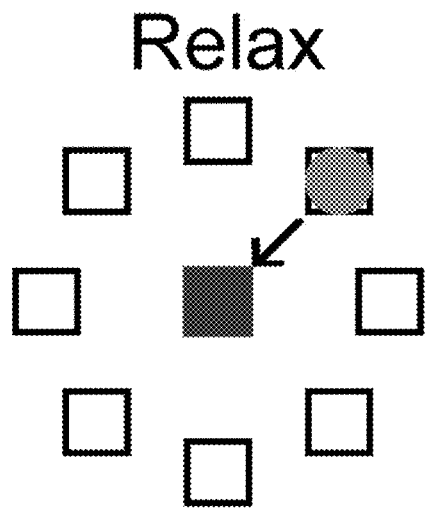
FIG. 2D depicts the embodiment of FIG. 2C, wherein subjects relax all muscles to permit the cursor to return to the original center position from an outer target position.
Figure 3A:
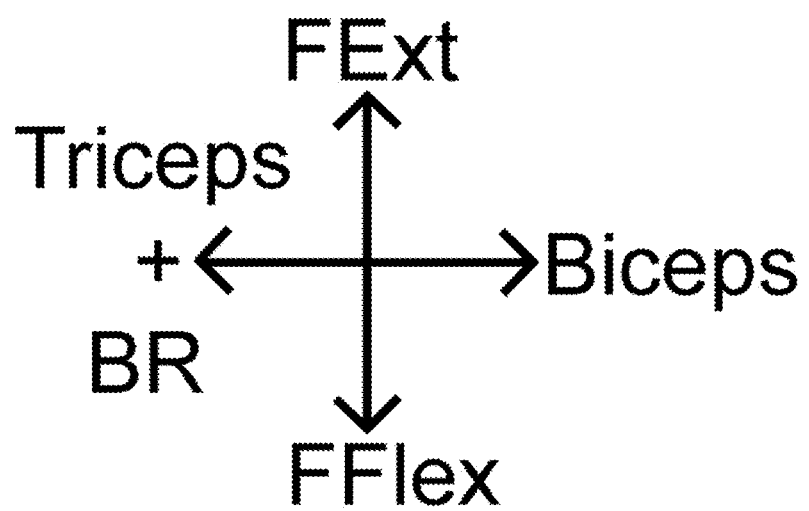
FIG. 3A depicts an embodiment of muscle mapping directions in an 8-target task for healthy subject groups. BR, brachioradialis; FFlex, flexor digitorum superficialis; FExt, extensor digitorum; ADelt, anterior deltoid; PDelt, posterior deltoid.
Figure 3B:
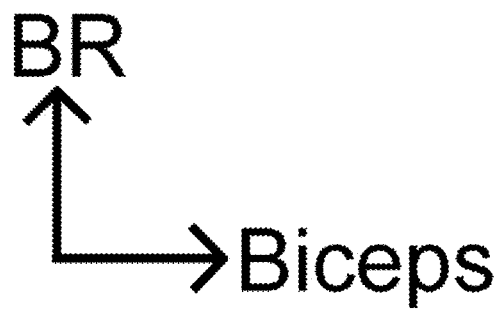
FIG. 3B depicts an embodiment of muscle mapping directions in a 2-target task for healthy subject groups. BR, brachioradialis.
Figure 3C:
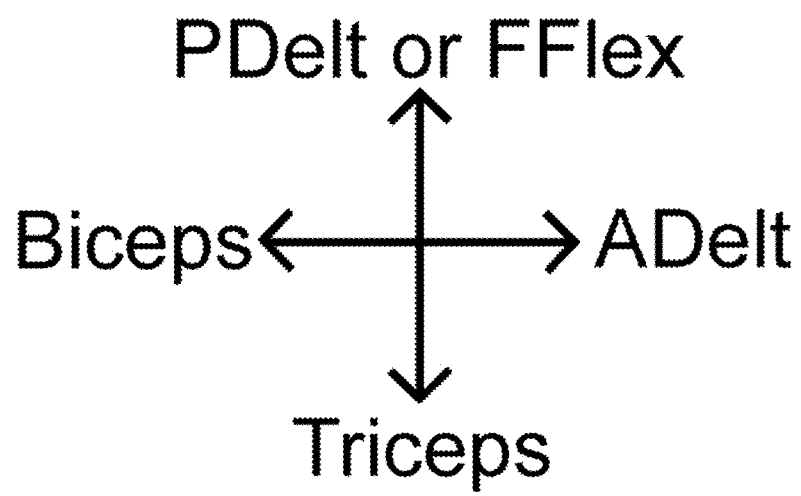
FIG. 3C depicts an embodiment of muscle mapping directions in an 8-target task for stroke subject groups. BR, brachioradialis; FFlex, flexor digitorum superficialis; FExt, extensor digitorum; ADelt, anterior deltoid; PDelt, posterior deltoid.
Figure 3D:
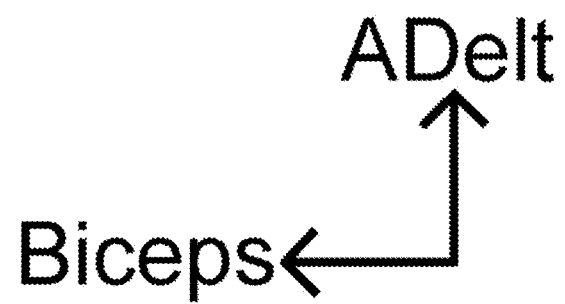
FIG. 3D depicts an embodiment of muscle mapping directions in a 2-target task for stroke subject groups. ADelt, anterior deltoid.

Referring to FIG. 1, one embodiment of the MCI device includes a myoelectric controller, a computer interface and a monitor. The myoelectric controller includes at least one muscle sensor and at least one data acquisition component. The at least one muscle sensor is selected from a surface sensor or an implantable sensor. The at least one muscle sensor is configured to record from at least one muscle of a subject. The myoelectric sensor communicates with a data acquisition component by either wired or wireless connection. The computer interface includes a computer readable medium that encodes at least one computer-implementable software program. The at least one computer implementable software program provides executable coding for generating a cursor image and at least one target image on the monitor. The at least one computer-implementable software program includes executable coding for generating a cursor icon as the cursor image, a first target position icon and a plurality of additional target position icons as the at least one target image on the monitor. The executable code of the at least one computer-implementable software program determines the real and monitor-visualized distance between the first target position icon and any one of the plurality of additional target position icons. Through executable code of the at least one computer-implementable software program, the movement of the cursor icon is controlled by at least one activation of at least one muscle of the subject. The executable code of the at least one computer-implementable software program translates the mapping of muscle activity to cursor icon movement. The executable code of the at least one computer-implementable software program also provides for independent task exercise routines and sub-routines for orthogonal or other mapping of co-activated muscles and their uncoupled activation.

The computer interface is in communication with the monitor. The monitor images icon movements and locations for the cursor icon, a first target position icon and a plurality of additional target position icons, wherein the at least one computer-implementable software program provides code that controls presentation of the aforementioned icon movements and locations on the monitor.

Cursor icon position can be derived in real time using EMGs from at least one muscle and preferably from a plurality of muscles (FIGS. 2A-D and 3A-D). Cursor control signals in at least two directions on an X-Y coordinate plane can be derived from surface EMGs by appropriate processing of recorded signals obtained with bipolar electrodes spaced apart. The locations of cursor icon position(s) can be scaled by a factor to enable cursor icon movement to a selectively imaged icon target at a relatively comfortable level of contraction of a subject's muscle. The typical 2-D position of the cursor icon on an X-Y coordinate plane is determined by the vector sum of the control signals derived from the EMG's. It is noted that 2-D orthogonal mapping of two co-activated muscles can be expanded to higher dimensional mapping space, such as 3-D orthogonal mapping of three co-activated muscles. Additionally, non-orthogonal mapping can be employed in the method, whereby one can map the movement of two or more muscles in non-orthogonal directions, such as, for example, directions 45 degrees apart.

Preferably, the location of the at least one muscle sensor is repositioned on, or remains positioned on, the at least one muscle in the same position from session to session involving use of the MCI device. For this purpose, a marking can be applied to a surface of the at least one muscle for replacement of one or more electrodes for subsequent sessions. Preferably, the marking can be made with a henna marker.

Because EMG activation signals can vary due to changes in electrode placement or possibly changes in skin impedance, it is desirable to adjust the muscle mapping gains between sessions so as to achieve comparable signal and subject effort level across different sessions. Within a given session, however, the gain is preferably maintained at a constant level for all trials during the session.

MCI Device—Method of Use: Training Muscle Movements

The MCI device can be used in the following manner. The at least one muscle sensor is attached to the surface of a limb of a subject. The subject is prompted to perform at least one task during each session. A task is one that prompts the subject to move the cursor icon to at least two predetermined target icon locations. Tasks can be of two forms: a training task that prompts the subject to move the cursor icon to at least two predetermined target icon locations; and a "generalization" task that prompts the subject to move the cursor icon to at least three or more predetermined target icon locations. Preferably, training tasks are configured to enable the subject to succeed at the task if they learned to decouple the co-activating muscles. The generalization tasks are configured to enable the subject to succeed if they could generalize the learned muscle decoupling to a different muscle mapping than that used in the training task.

Both task types prompt a subject to maintain a cursor icon position over a predetermined target icon position for a unit of time. The maintenance of the cursor icon position is controlled by the subject invoking at least one muscle contraction to effect movement (or lack thereof) of the cursor icon. In one embodiment, the subject must maintain the cursor icon position over a first predetermined target icon position before the first predetermined target icon position disappears and a second predetermined target icon position appears. Preferably, the first predetermined target icon position and second predetermined target icon position differ in position on an X-Y coordinate plane, as imaged on the computer monitor. Thereafter, the subject is prompted to invoke at least one muscle contraction to effect movement of the cursor icon to a position over the second predetermined target icon position.

By mapping the muscles in orthogonal directions in the training task, the subject can learn to uncouple co-activating muscle movements, whether normal or abnormal in muscle function. Importantly, requiring a subject move the cursor along orthogonal axes (for example, along a horizontal axis and a vertical axis) during the task routines and sub-routines provides the requisite training to uncouple co-activated muscles and their movements. The task difficulty can be varied in multiple ways by altering parameters in the MCI device task. For example, the distances between any members of the plurality of target icon positions can be varied during a given session and/or between sessions. By varying the distances between any members of the plurality of target icon positions, the subject is prompted to actuate muscles to move the cursor icon to the new location of the member of the plurality of target icon positions. Likewise, the size of the target icon can also be varied within a given session and/or between sessions. By varying the target icon size, the difficulty of the task can be adjusted to suit the subject's progress.

The subject's interest in the method of using the MCI device can be enhanced by enabling the at least one computer-implementable software program to provide subject-interactive functionality. Such subject-interactive functionality can take the form of skill challenges, gaming, progression scales, encouragement mechanisms, inspirational algorithms and the like. The advantage to the subject engaged in one or more subject-interactive functionalities is to promote engagement of the subject in using the MCI device for the disclosed method for the benefit of the subject.

Healthy Subjects: Task Performance and Reduction of Co-Activation

Figure 4A:
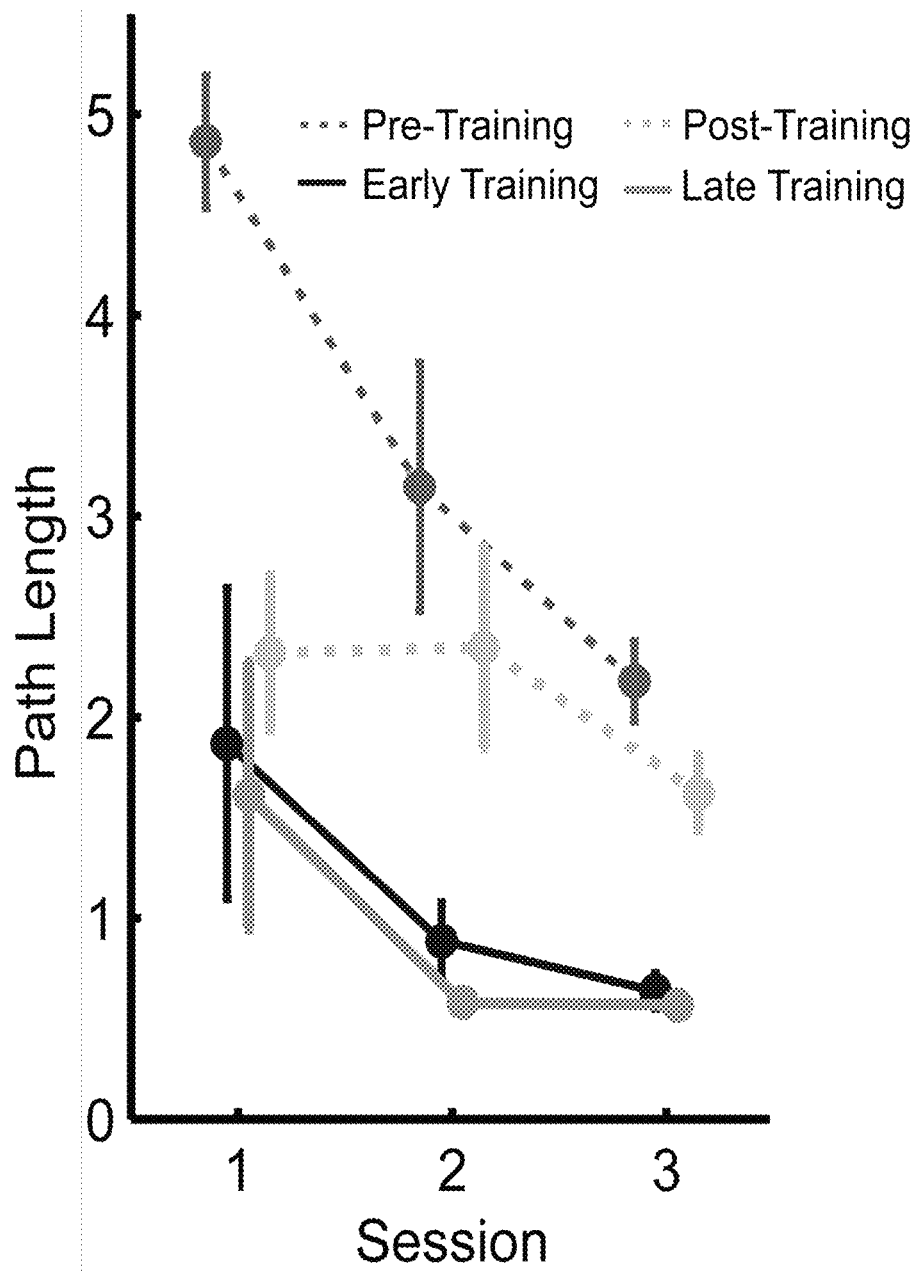
FIG. 4A depicts an embodiment of healthy subjects' task performance changes in path length measures, as averaged across all subjects for pre- and post-training (dashed lines) and early and late training (solid lines). Error bars represent standard error (SE).
Figure 4B:
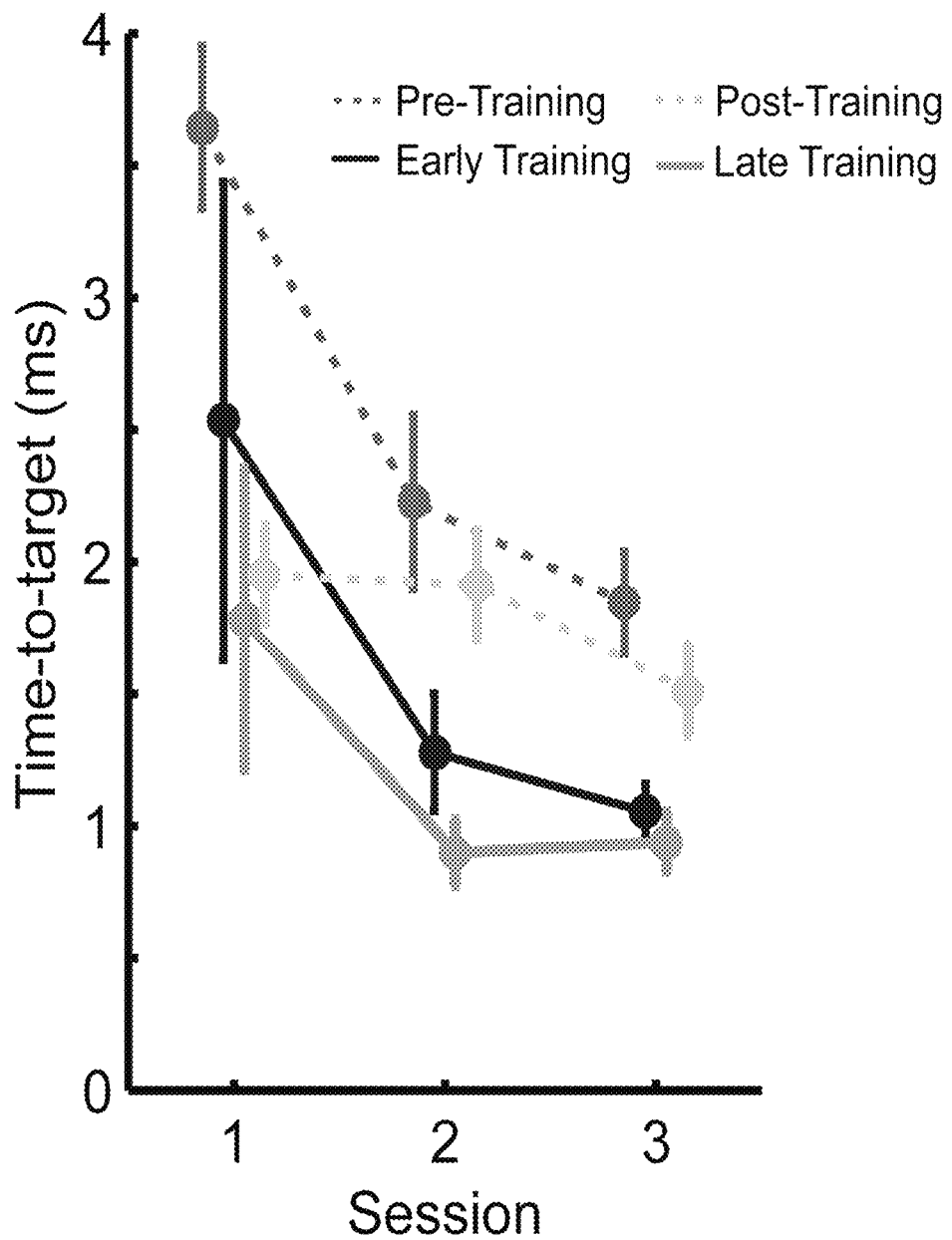
FIG. 4B depicts an embodiment of healthy subjects' task performance changes in time-to-target measures, as averaged across all subjects for pre- and post-training (dashed lines) and early and late training (solid lines). Error bars represent standard error (SE).

Referring to FIG. 4, the ability of healthy subjects to learn to control the MCI device in tasks was investigated. Subjects learned the training task quickly, as evidenced by the rapid improvements in path length (FIG. 4A solid lines) and time-to-target (FIG. 4B solid lines) from session 1 to 2. Path length (PL) improved by 69% ($\Delta PL=-1.3\pm0.8$, p=0.17, paired t-test) and time-to-target (TT) improved by 62% ($\Delta TT=-1.59\pm0.9$ s, p=0.16) from early training in session one to late training in session three. They learned the 8-target task quickly as well (dashed lines, FIG. 4A-B). The performance improvement in both tasks persisted for one week.

Figure 5:
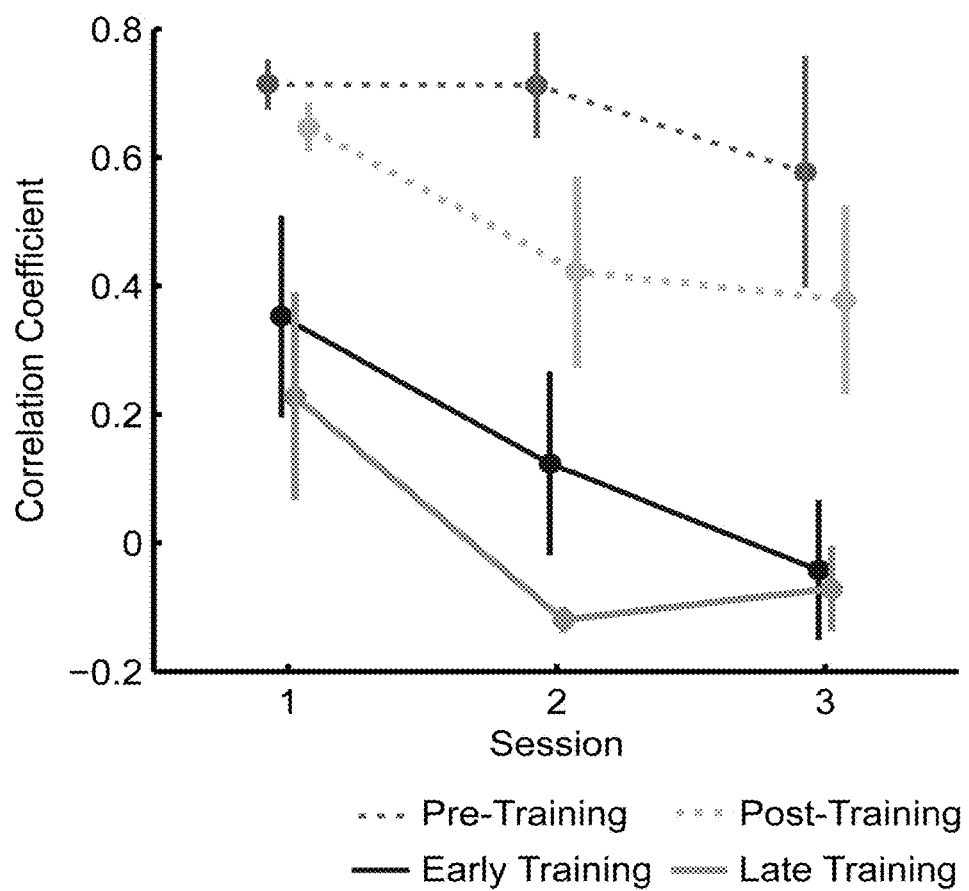
FIG. 5 depicts an embodiment of changes in healthy subjects' co-activation, wherein mean correlation coefficients between biceps and brachioradialis activity during the training (solid lines) and pre- and post-training tasks (dashed lines) are presented and showed that correlation decreased within a session during training.
Figure 6A:
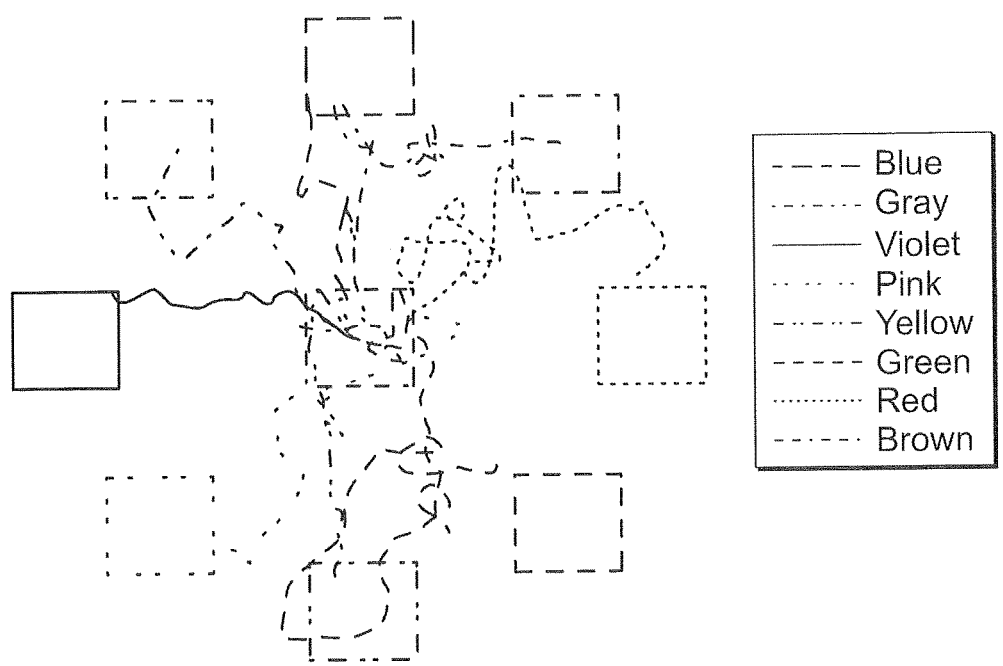
FIG. 6A depicts one embodiment of mean movement trajectories and representative EMG traces from a stroke subject, wherein the subject's average trajectories of cursor movement to each target during pre-training in the first session are presented. Blue and red trajectories represent cursor movement in the biceps direction and anterior deltoid direction, respectively.
Figure 6B:
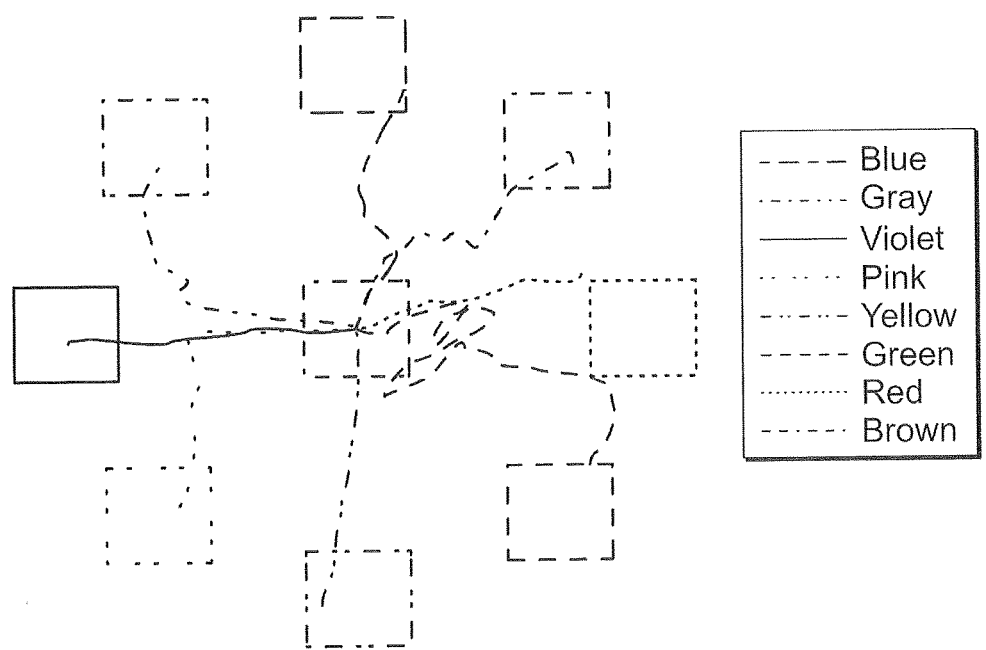
FIG. 6B depicts one embodiment of mean movement trajectories and representative EMG traces from a stroke subject, wherein the subject's average trajectories of cursor movement to each target during post-training in the last session are presented. Blue and red trajectories represent cursor movement in the biceps direction and anterior deltoid direction, respectively.
Figure 6C:
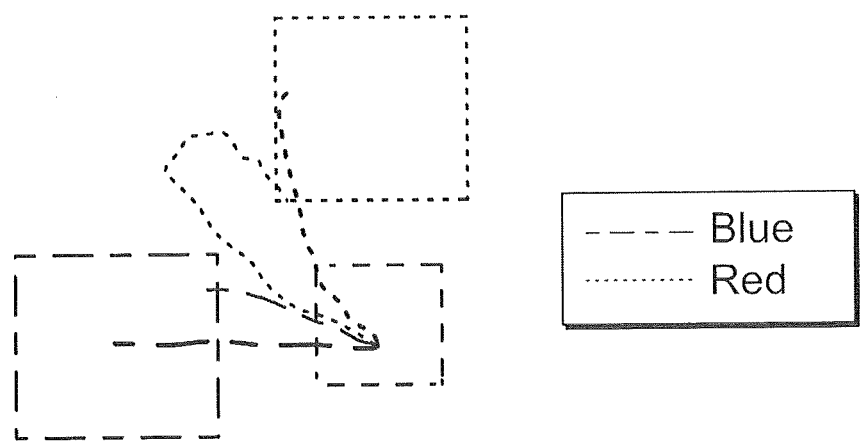
FIG. 6C depicts one embodiment of mean movement trajectories and representative EMG traces from a stroke subject, wherein the subject's average trajectories of cursor movement to each target during early training in the first session (thin lines) and late training in the last session (thick lines) are presented. Blue and red trajectories represent cursor movement in the biceps direction and anterior deltoid direction, respectively.
Figure 6D:
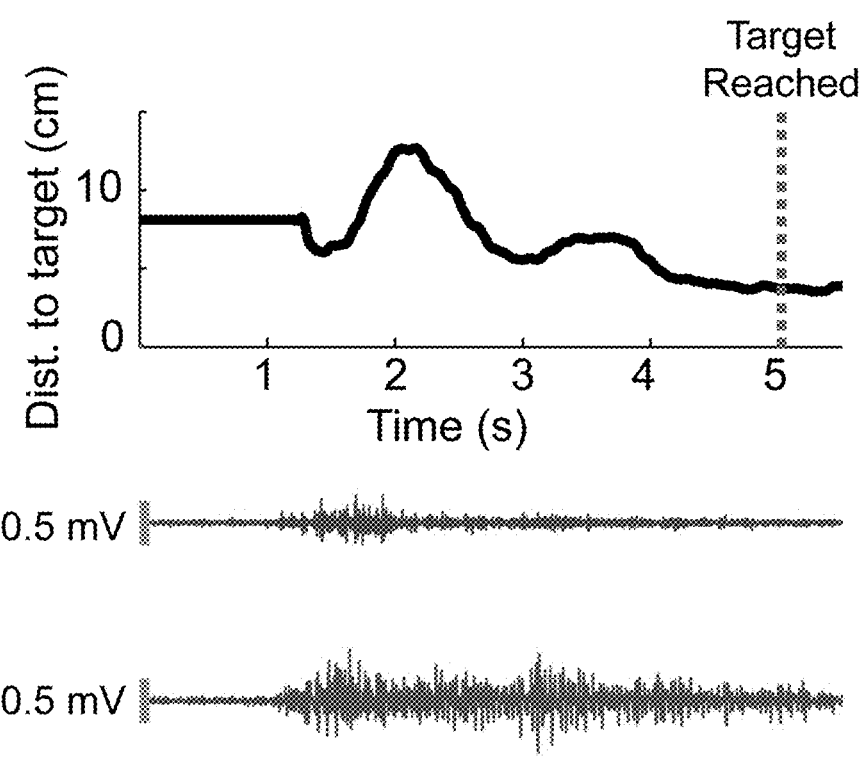
FIG. 6D depicts an exemplary plot of time (sec) vs. distance to target (cm) that shows the time to reach target (vertical dashed line), and representative EMG traces of biceps (blue) and anterior deltoid (red) for single trials during movement in the anterior deltoid target direction for early training in the first session. Vertical gray bars in the EMG traces represent EMG scale (0.5 mV).
Figure 6E:
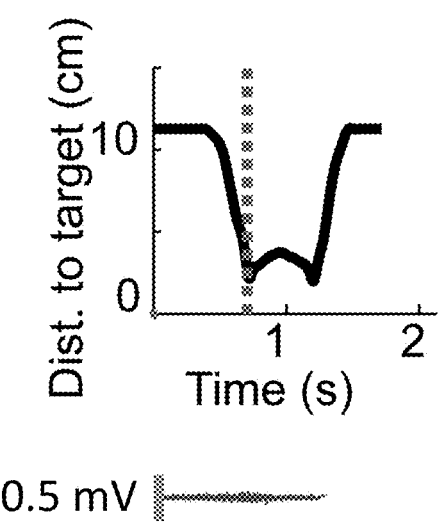
FIG. 6E depicts an exemplary plot of time (sec) vs. distance to target (cm) that shows the time to reach target (vertical dashed line), and representative EMG traces of biceps (blue) and anterior deltoid (red) for single trials during movement in the anterior deltoid target direction for late training in the last session. Vertical gray bars in the EMG traces represent EMG scale (0.5 mV).
Figure 6F:
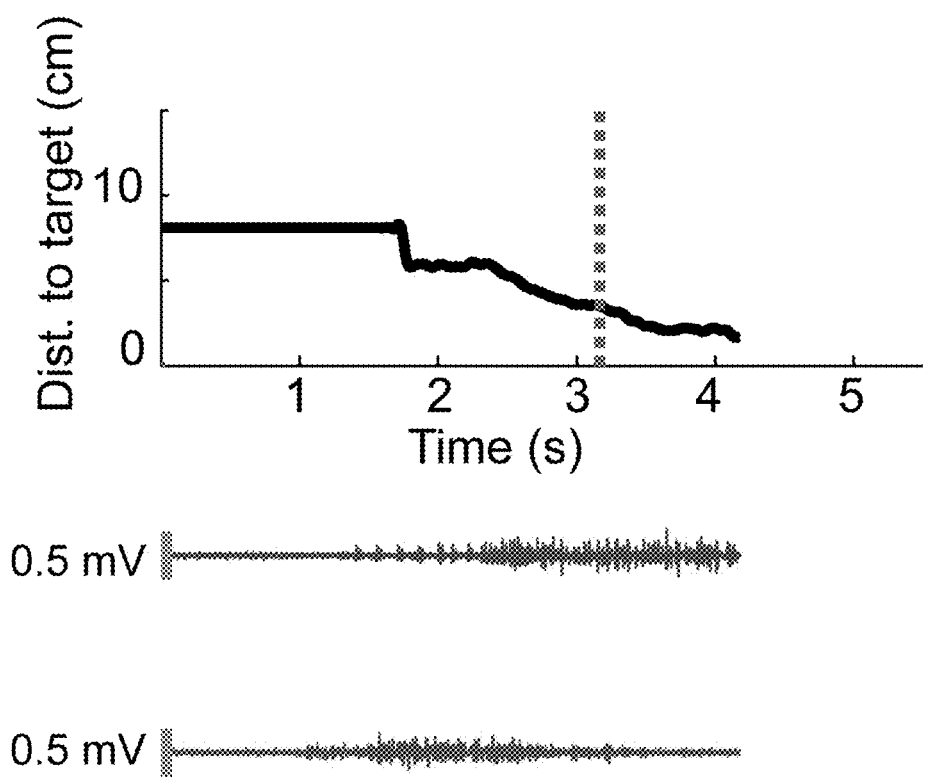
FIG. 6F depicts an exemplary plot of time (sec) vs. distance to target (cm) that shows the time to reach target (vertical dashed line), and representative EMG traces of biceps (blue) and anterior deltoid (red) for single trials during movement in the biceps target direction for early training in the first session over time. Vertical gray bars in the EMG traces represent EMG scale (0.5 mV).
Figure 6G:
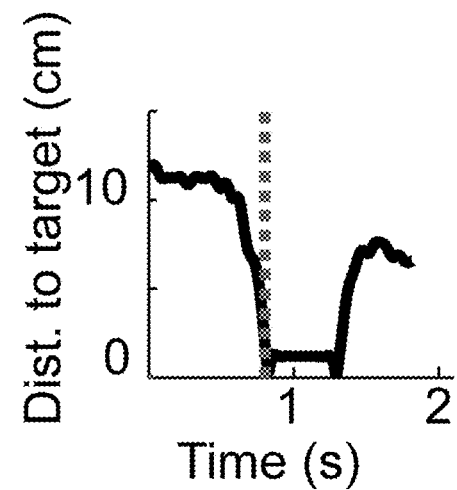
FIG. 6G depicts an exemplary plot of time (sec) vs. distance to target (cm) that shows the time to reach target (vertical dashed line), and representative EMG traces of biceps (blue) and anterior deltoid (red) for single trials during movement in the biceps target direction for late training in the last session over time. Vertical gray bars in the EMG traces represent EMG scale (0.5 mV).
Figure 6G:
Figure 6G:

Referring to FIG. 5, healthy subjects readily learned the task of decoupling biceps and brachioradialis muscles within 2 sessions on consecutive days. During the training task, correlation between these muscles decreased by an average ($\pm$SE) of $0.42\pm0.18$ from early training in session one to late training in session three, although this difference did not quite reach significance (p=0.055). Correlation decreased significantly from the pre-training phase of session one to the post-training phase of session three ($\Delta R=-0.33\pm0.12$, p=0.046).

Stroke Subjects: Task Performance

Referring to FIG. 6A-G, in the 2-target training task, steady learning was observed, with substantial improvements between early training in the first session and late training in the final session ($\Delta SR=15\pm5\%$, p=0.03; $\Delta TT=-1.9\pm0.5$ s, p=0.01; $\Delta PL=-1.3\pm0.5$, p=0.056).

Stroke Subjects: Reduction of Co-Activation

Figure 7A:
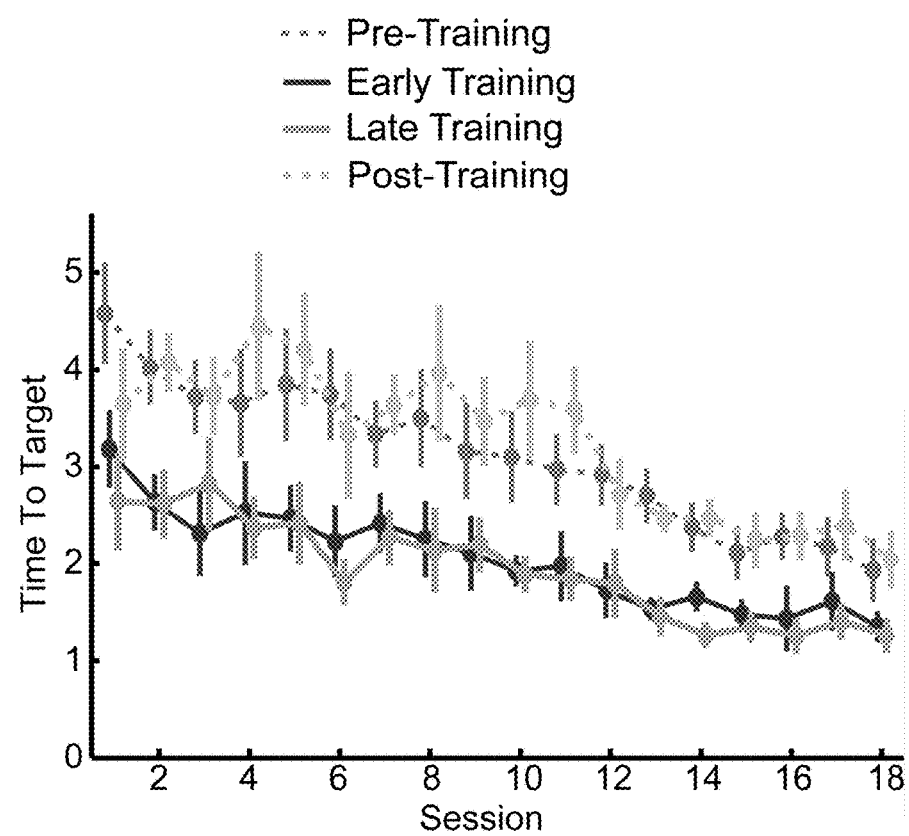
FIG. 7A depicts an embodiment of stroke subjects' task performance changes wherein performance measures directed to time-to-target, as averaged across all subjects during both training (solid lines) and pre- and post-training (dashed lines) tasks.
Figure 7B:
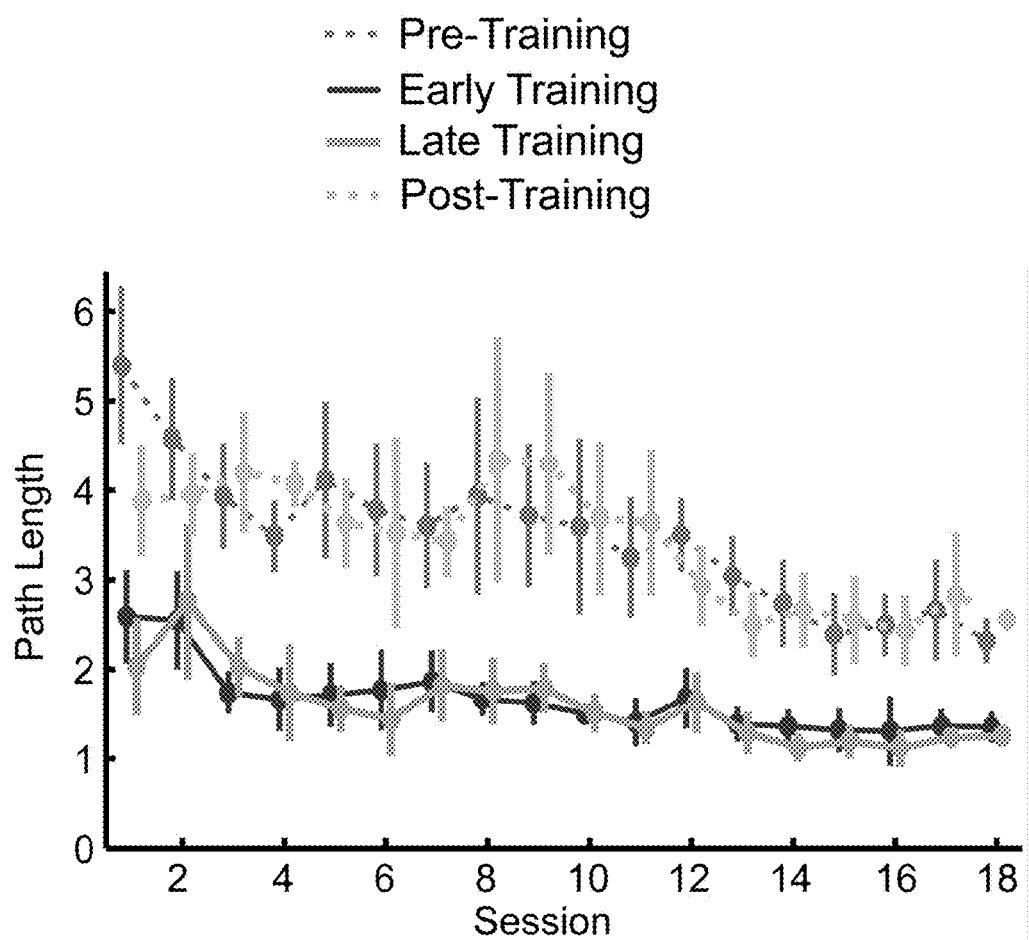
FIG. 7B depicts an embodiment of stroke subjects' task performance changes wherein performance measures directed to path length, as averaged across all subjects during both training (solid lines) and pre- and post-training (dashed lines) tasks.
Figure 7C:
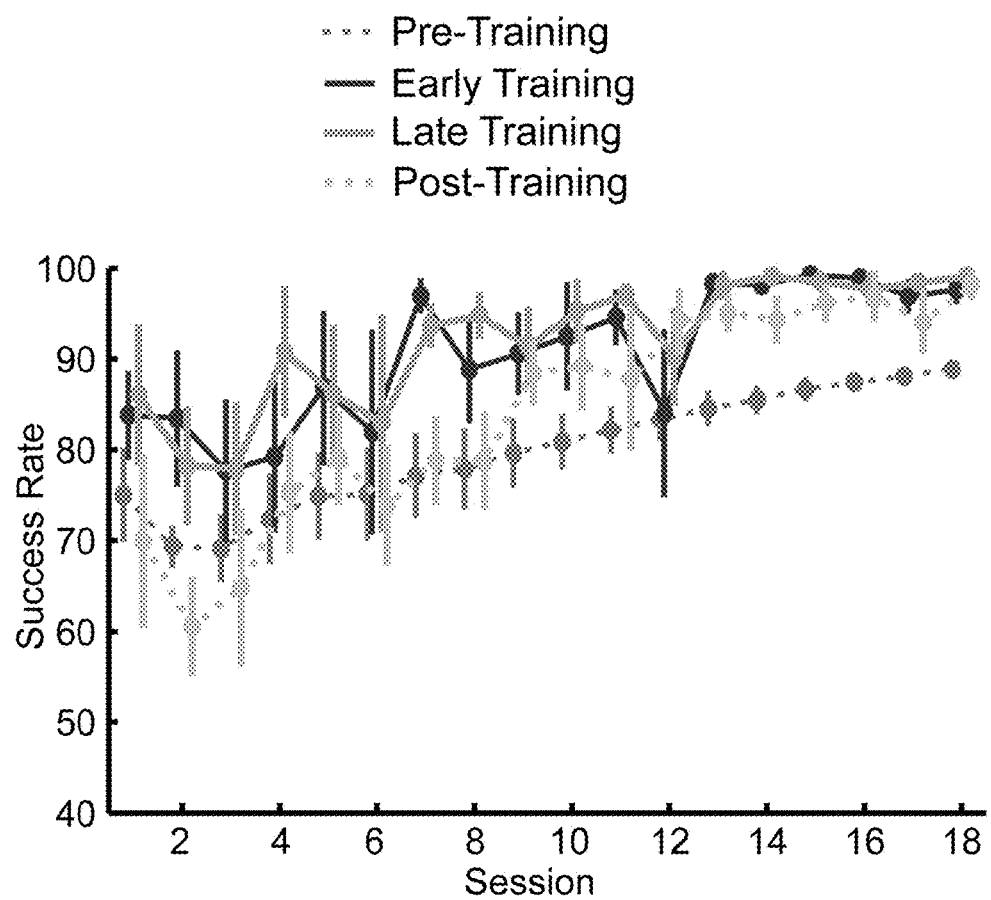
FIG. 7C depicts an embodiment of stroke subjects' task performance changes wherein performance measures directed to success rate, as averaged across all subjects during both training (solid lines) and pre- and post-training (dashed lines) tasks.

Referring to FIG. 7A-C, the 2-target training task required stroke survivors to learn to reduce co-activation in order to succeed. While performing this task, stroke subjects steadily improved their ability to decouple biceps and anterior deltoid EMGs (FIG. 7A,B). Correlations between the two muscles steadily decreased with practice and declined by an average of 97% ($\Delta R=-0.45\pm0.08$, p=0.005) between early training of the first session and late training of the last session. Muscle correlations during pre- and post-training decreased by 29% ($\Delta R=-0.19\pm0.15$, p=0.30, FIG. 7C).

Stroke Subjects: Muscle Tuning Curves

Figure 8A:
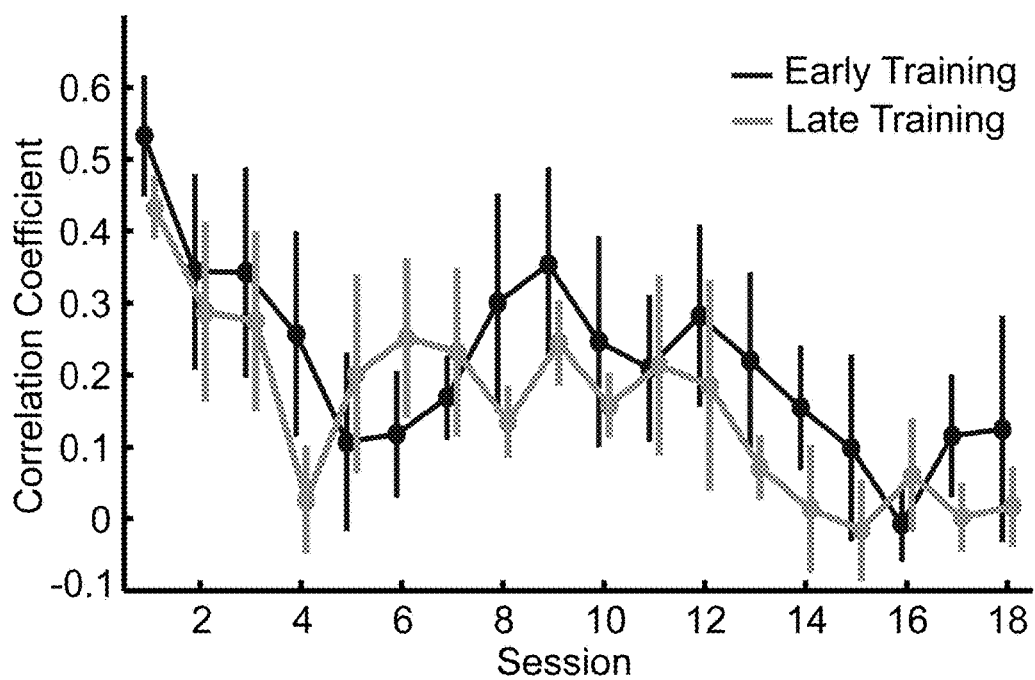
FIG. 8A depicts one embodiment of changes in stroke subjects' co-activation, wherein the mean correlation coefficients between biceps and anterior deltoid activity during the training tasks are shown.
Figure 8B:
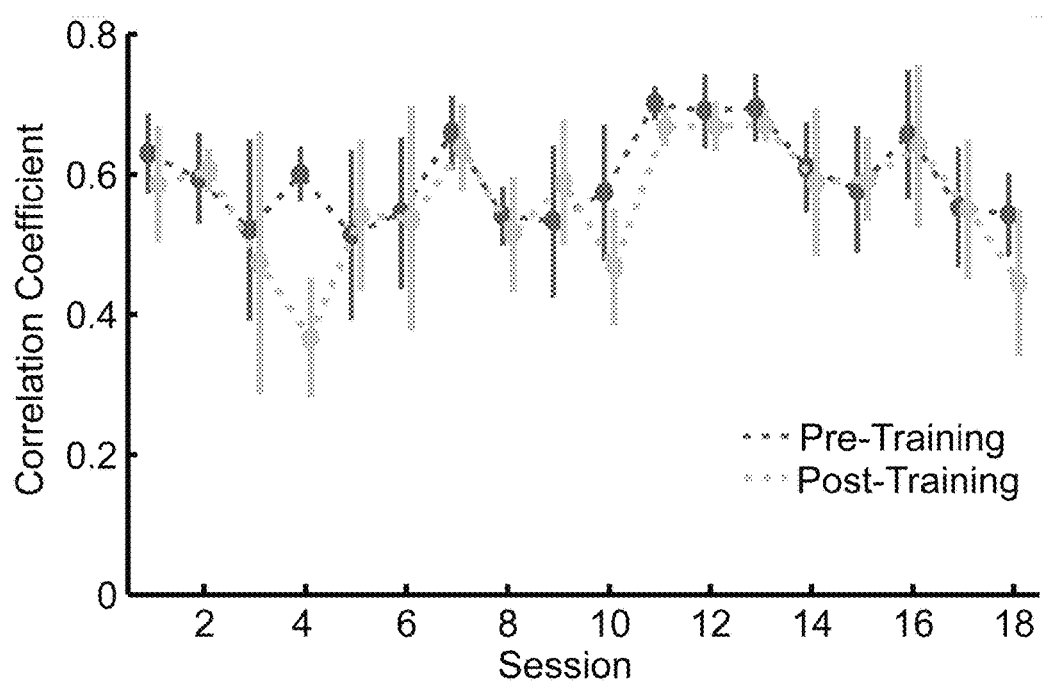
FIG. 8B depicts one embodiment of changes in stroke subjects' co-activation, wherein the mean correlation coefficients between biceps and anterior deltoid activity during the pre- and post-training tasks are shown.
Figure 9A:
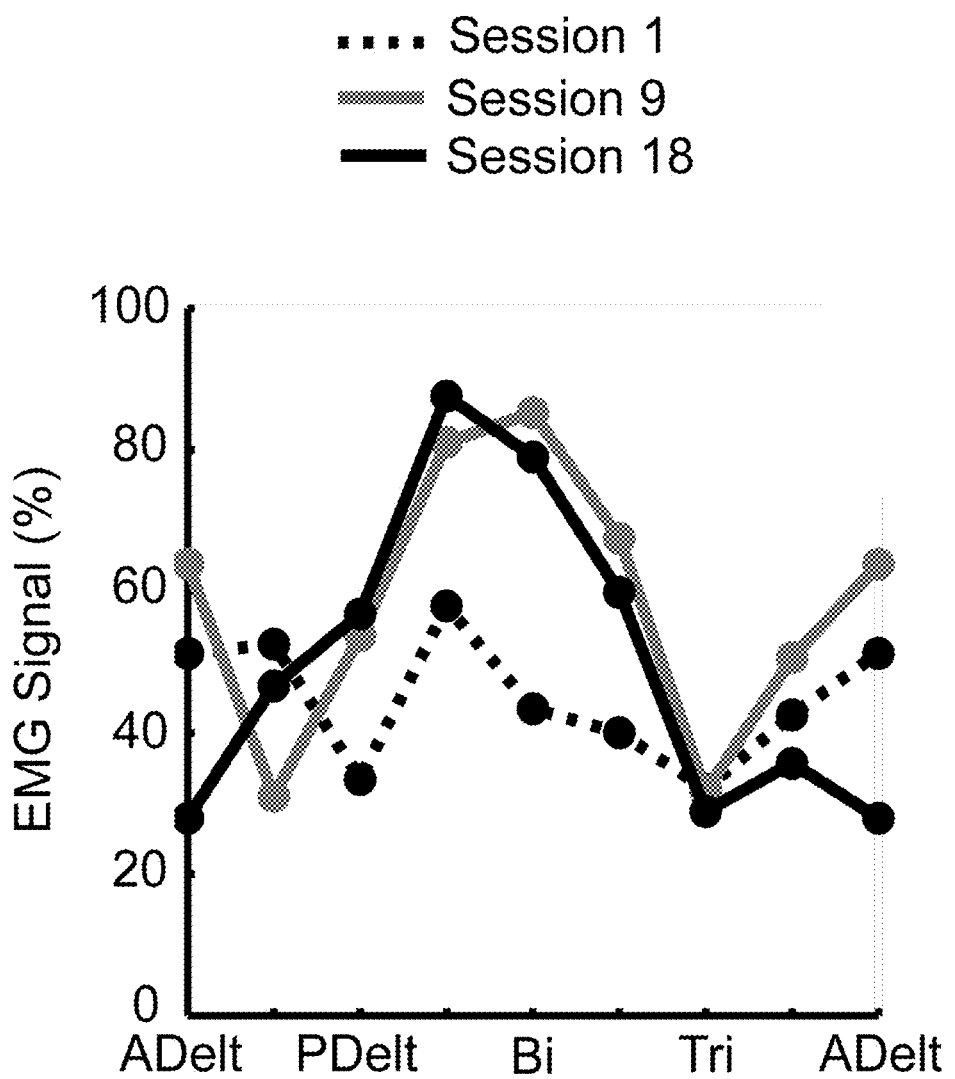
FIG. 9A depicts one embodiment of the evolution of muscle tuning curves over time in stroke subjects, wherein muscle tuning curves of biceps averaged across subjects from post-training tasks of the first (dashed line), ninth (gray line), and last (black line) sessions are shown. Control signals are normalized to the maximum level in both sessions and averaged across trials during the hold period. Key: ADelt, anterior deltoid; PDelt, posterior deltoid; Bi, biceps; Tri, triceps.
Figure 9B:
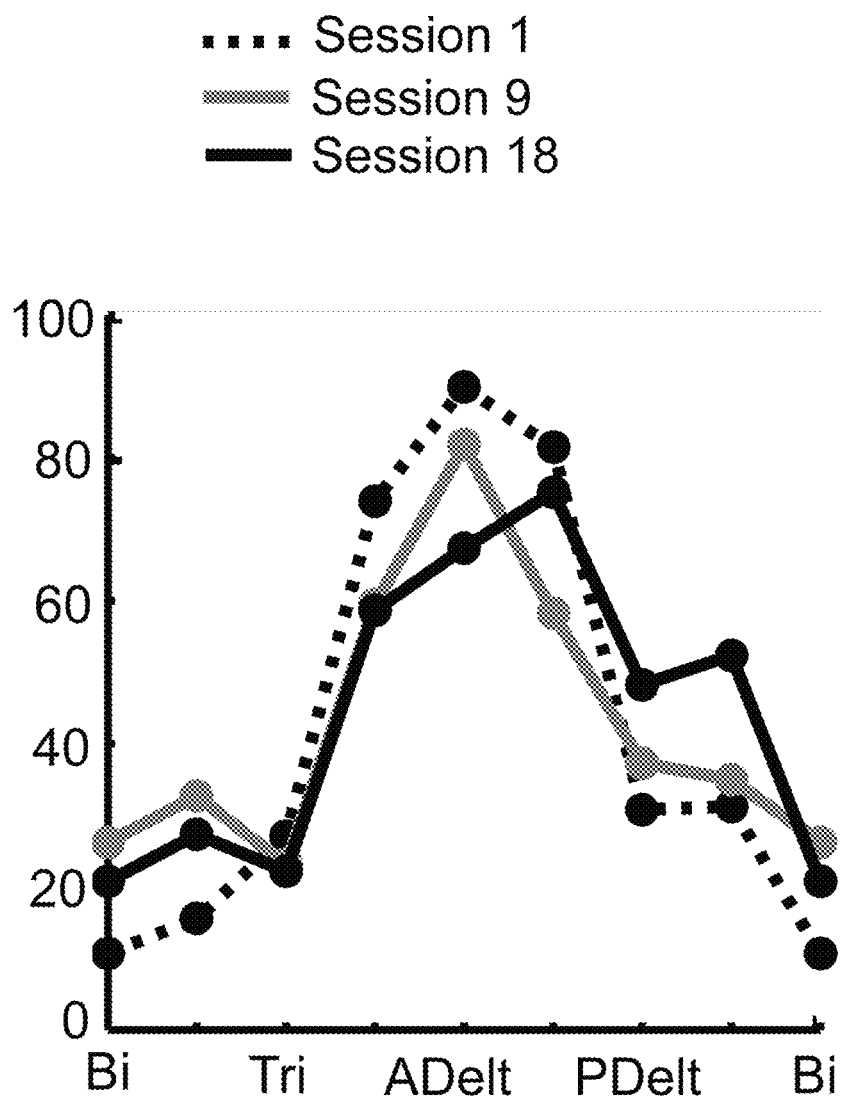
FIG. 9B depicts one embodiment of the evolution of muscle tuning curves over time in stroke subjects, wherein muscle tuning curves of anterior deltoid averaged across subjects from post-training tasks of the first (dashed line), ninth (gray line), and last (black line) sessions are shown. Control signals are normalized to the maximum level in both sessions and averaged across trials during the hold period. Key: ADelt, anterior deltoid; PDelt, posterior deltoid; Bi, biceps; Tri, triceps.
Figure 9C:
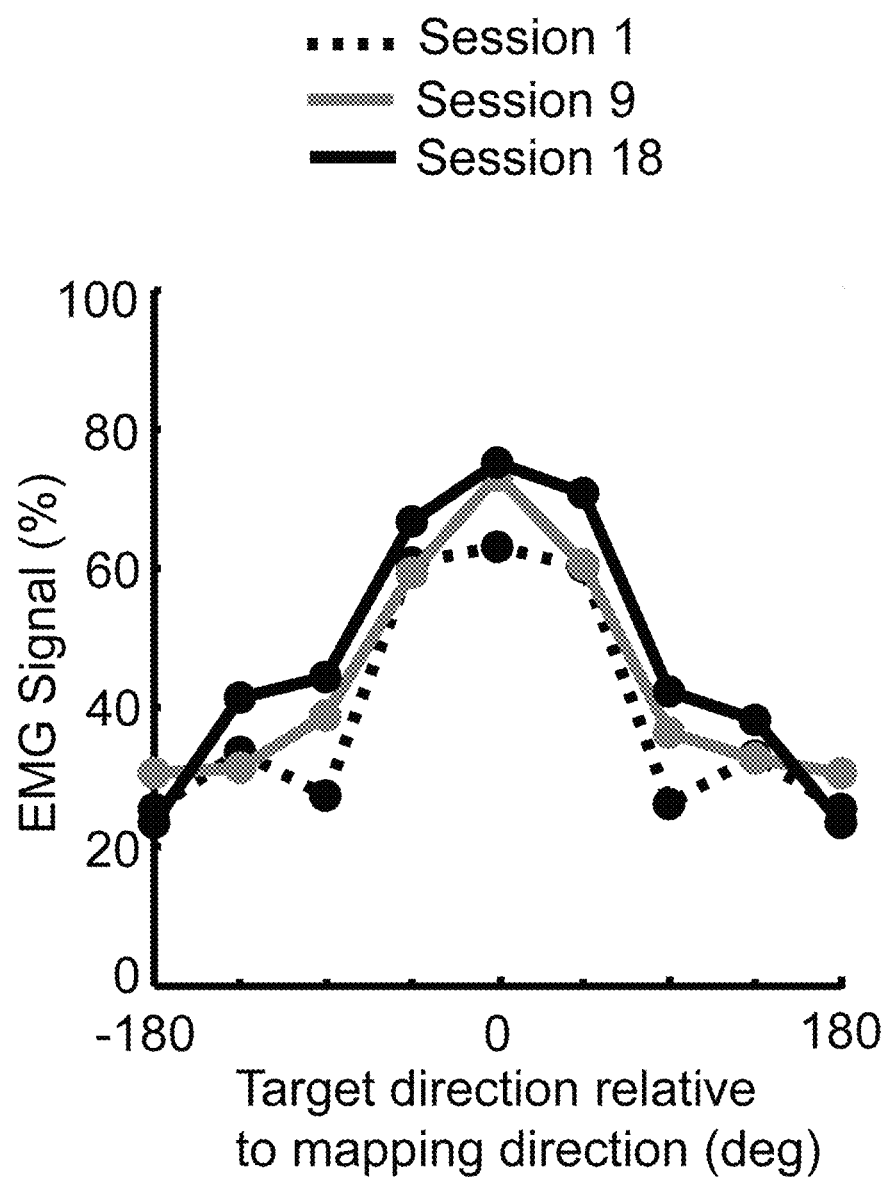
FIG. 9C depicts one embodiment of tuning curves averaged across all 4 muscles (that is, anterior deltoid, posterior deltoid, bicep, and triceps) and subjects during post-training over sessions. Curves were aligned to the appropriate direction before averaging across muscles and subjects.

Referring to FIGS. 8A-B and FIG. 9A-C, muscle tuning curves for changes across sessions were examined in stroke subjects to further investigate how stroke subjects used muscles to control cursor movement. The average tuning curves across all stroke subjects clearly show that biceps activity increased its tuning toward the appropriate mapping direction and adjacent targets (FIG. 8A and FIG. 9A). Anterior deltoid initially was tuned predominantly in the appropriate direction and therefore did not change by a large amount (FIGS. 8B and 9B). When averaged over all muscles and subjects, a gradual increase in tuning depth (the peak-to-trough distance) in the appropriate mapping direction was seen over time (FIG. 9B).

Effects of Training on Arm Function

Four stroke subjects reported subjective improvement of arm or hand function in activities of daily living, including bathing, dressing, and washing dishes, during the study period. All stroke subjects enjoyed performing the MCI device and training method, but said it could be made even more enjoyable by integrating with a video game during training sessions using the MCI device and method. Four of five asked for a larger dose of training and the remaining subject said the dose was just about right. Three subjects displayed improvement in FMA-UE scores by 3 points each, while the other two subjects did not improve their scores. Reduced impairment correlated with reduced co-activation during training: $\Delta R=-0.52\pm0.11$ vs. $-0.34\pm0.09$ for subjects whose FMA-UE scores did and did not improve, respectively.

The pathophysiology of abnormal co-activation is poorly understood, and there exists evidence, mostly indirect, to support origins both in increased bulbospinal outflow and in cortex. It is also unclear whether abnormal synergies are fixed and simply augmented by therapy or can be changed. The results disclosed herein suggest that they may be malleable.

The MCI device and method provide specific and intuitive feedback to the subject about their muscle activity. This disclosure demonstrates for the first time the ability to directly decouple muscle activations in this patient population. The MCI device and method provides intuitive feedback about the co-activation that only allows success when the muscles are decoupled. This can allow users to concentrate solely on succeeding in the task without explicitly thinking about activating individual muscles, which could take advantage of implicit motor learning mechanisms. Implicit motor learning is necessary for behavioral improvement, more durable over time, and less attentionally demanding than explicit learning. Furthermore, since the method of using the MCI device only requires EMG activity, rather than production of substantial forces, the method can be used with severely-impaired stroke survivors. This implementation is critical, since these patients are often excluded from rehabilitative trials and are less likely to benefit from conventional therapy due to their extremely limited movement.

These results support use of the MCI device and method as a clinical treatment.

EXAMPLES

Example 1. Subjects

Five right-handed subjects (4 men, 1 woman, ages 23-27) free from neurological and musculoskeletal disorders and five subjects (1 man, 4 women, ages 50-58) whose stroke occurred 1.5-25 years prior to enrollment participated in this study. All subjects gave informed consent. This study was approved by the Northwestern University Institutional Review Board. Stroke survivors were included who had 1) hemiparesis with moderate to severe impairment of the affected arm (equivalent to a score of 12-40 on the upper-extremity portion of the Fugl-Meyer Motor Assessment, FMA-UE), 2) exhibited co-activation of the biceps and anterior deltoid muscles determined by clinical observations during FMA-UE assessment and subjects' performance on the MCI during the initial screening process, and 3) a single, unilateral, ischemic stroke at least 1 year prior to enrollment. Stroke survivors were excluded who had 1) significant acute or chronic pain in the upper limbs or spine, 2) greater than minimal sensory loss in the affected upper arm, 3) moderate to severe vision loss, 4) cognitive impairment severe enough to affect digit span and understanding of task-related instructions, and 5) participated in another arm-motor study within 30 days of the start of this study. Subjects were allowed to continue their usual exercise or physical therapy regimens, but not allowed to start a new regimen during the study. All stroke subjects that participated had right-sided hemiparesis (FMA-UE score 19±3, mean±SD).

Example 2. Behavioral Task

Subjects sat in a chair with their right arm supported by an armrest. Healthy subjects' arms were held in a semi-pronated position (to make it more difficult to decouple biceps and brachioradialis) and immobilized with cushioned restraints at the hand, wrist and upper forearm. Stroke subjects' impaired arms were held in a prone position. A monitor in front of the subjects displayed a cursor (yellow circle with a radius of 1.5 cm) and red square target of comparable size (FIG. 1).

Subjects performed isometric contractions of multiple muscles to move the cursor from a target in the center of the screen to a randomly-presented target near the outer edge of the monitor—a modified center-out task (FIG. 2A-D). Activation of each muscle was mapped to one of four directions within the 2-D cursor space (see Muscle Mapping). The center target corresponded to zero net muscle activation (resting position). After the cursor was held in the center target for 512 ms, an outer target appeared and the center target disappeared, signaling the start of a trial. Outer targets were located at a distance of 12 cm from the center target in all sessions except the first 5 and first 2 sessions for subjects 1 and 2, respectively; in these first few sessions they were located 7 cm from the center. (The distance was increased to make the task more challenging after it was seen to be too easy for these subjects.) When the cursor reached the outer target it changed color, and subjects were required to hold the cursor there at least 32 ms to achieve a successful trial.

Example 3. Cursor Control Signal

A cursor position in real time was derived using EMGs from multiple arm muscles. Surface EMG was recorded with bipolar electrodes spaced 1 un apart, amplified with a gain of 1000 (Delsys Bagnoli EMG System), digitally sampled at 1 kHz (National Instruments USB-6229) and continuously collected in real-time using a customized program in the BCI2000 software platform, which also controlled the behavioral feedback. The control signals in each direction were derived from EMGs by low-pass filtering at 500 Hz, rectifying, high-pass filtering at 20 Hz, and then convolving with a 400-ms rectangular window. The electrode positions were marked at the end of the session with a henna marker to ensure the same location in the next session. At the start of each session, subjects were instructed to produce two maximum voluntary contractions (MVCs) of each muscle independently. The control signals were scaled by a factor that allowed cursor movement to the targets at a relatively comfortable level of contraction (~42% of the MVC). Since EMG activation levels sometimes varied due to slight changes in electrode placement or skin impedance, the gains sometimes changed across sessions, to make the effort level similar across sessions. However, the gains remained the same across all trials within each session. The vector sum of the control signals determined the 2-D cursor position.

Example 4. Muscle Mapping

Each subject performed two tasks in each session: a training task that used 2 outer targets and a generalization task that used 8 outer targets. In the training task, the two co-activating muscles (biceps brachii and brachioradialis for healthy subjects, anterior deltoid and biceps brachii for stroke survivors) were mapped to orthogonal directions and only these signals were used in the summed control signal (FIG. 3A-D); thus, subjects could only succeed in the task if they learned to decouple the co-activating muscles. An 8-target task was also designed to assess the extent to which subjects could generalize the learned decoupling. In the 8-target task, the two co-activating muscles were mapped in opposite horizontal directions. In healthy subjects, an independent muscle (triceps) was added in the direction of brachioradialis to make generalization of the task more challenging. Two independent muscles (flexor and extensor digitorum superficialis for healthy subjects, triceps and either posterior deltoid or flexor digitorum superficialis in stroke subjects) were mapped in opposite vertical directions. Cursor movement to targets located along the diagonals was achieved by simultaneous activating the two muscles mapped to the adjacent directions. At the beginning of the experiment, subjects were informed of the specific directions corresponding to activation of each recorded muscle (mapping direction, FIG. 3A-D).

In some stroke subjects, the affected muscles retained some spontaneous muscle activity (mainly in biceps and flexor digitorum) when trying to relax, which prevented the cursor from reaching the center target. Therefore, the baseline activity was averaged for each muscle within a 0.5-s window starting 1 s after the completion of a trial and subtracted from the corresponding control signals for the next trial.

Example 5. Experimental Method

Healthy subjects participated in three sessions separated up to one week (days 0, 1, and 6). In each session, they performed 10 minutes of the 8-target task (pre-training), followed by 20 minutes of the training task, and then 10 minutes of the 8-target task (post-training). For analysis, the first and last 2.5 minutes of training were denoted early and late training, respectively. Stroke subjects participated in three sessions per week for 6 weeks. In each session, they performed 10 minutes of the pre-training task, 30 minutes of the training task, and another 10 minutes of the post-training task. For analysis, the first and last 5 minutes of training were denoted early and late training, respectively. Performance and outcome measures Subjects' performance in controlling the MCI device was evaluated via three different metrics. The first was the success rate, defined as the percentage of targets successfully acquired (i.e. cursor entered the intended target). The second was time to target (TT), defined as the interval between the appearance of the outer target and the time the cursor successfully entered the intended target. The third was path length (PL), defined as the cumulative distance the cursor traveled in each trial, normalized by the straight-line distance between the center and outer targets.

The level of co-activation between muscles as the Pearson correlation coefficient (R) between the filtered EMGs (control signals) was defined. The R value was computed during the period from the appearance of outer target to the end of the outer target hold time on consecutive trials that were concatenated. The correlation levels across sessions were compared to assess leaning, and across tasks, to assess whether the change in co-activation generalized. Success metrics and R values were computed during early training and late training periods, as well as during the 10-minute pre- and post-training periods. Statistical significance was determined using paired t-tests.

To investigate the contribution of each muscle to movement to each target in more detail, the muscle tuning curves were computed. Tuning curves were computed from the average control signal during the outer target hold period for each trial during the 8-target post-training task. Tuning curves were aligned to the mapping direction of each muscle. The changes in these curves across sessions were evaluated.

Finally, FMA-UEs were evaluated before the first session and at the end of the last session to assess the extent of improvement due to the MCI training. Subjects after the study were surveyed using the following four questions: 1) Did you notice any improvement in your arm function during the study? If so, what improved? 2) Was the amount of training too little, too much, or just right? 3) Did you enjoy participating in the study? 4) How would you recommend changing the MCI training paradigm to make it more enjoyable?

Exemplary performance attributes of the MCI device and method of use with subjects are summarized in Table 1.

Terminology and Definitions

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

Terms used herein are intended as "open" terms (e.g., the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

TABLE 1

Details of performance changes[a]

| Participant | ΔR 2-Target | ΔR 8-Target | Initial FMA | ΔFMA | Participants' Observations of | |
|---|---|---|---|---|---|---|
| | | | | | Improved FMA Items | Improved Movement |
| 1 | −0.52 | −0.21 | 19 | +3 | Shoulder abduction/adduction, elbow flexion/extension | Improved arm function when washing dishes |
| 2 | −0.44 | 0.33 | 18 | +3 | Shoulder external rotation and adduction, elbow extension | Improved arm range of motion and increased ability to move |
| 3 | −0.83 | −0.61 | 23 | +3 | Elbow and shoulder flexion, mass flexion (power grasp) | Improved hand function |
| 4 | −0.42 | −0.26 | 20 | 0 | — | — |
| 5 | −0.36 | −0.17 | 14 | 0 | — | Increased arm use, improved arm function when bathing |

Abbreviation: FMA-UE, upper-extremity portion of the Fugl-Meyer Motor Assessment.
[a]Shown are changes in R (ΔR) from the first to the last session during training (2-target), before to after training (8-target), initial and change in FMA-UE scores, the items in the FMA that improved for each participant, and the participants' reports of functional improvement in the survey.

It should be understood that the methods, procedures, operations, devices, and systems illustrated in FIGS. 1 through 9 may be modified without departing from the spirit of the present disclosure. For example, these methods, procedures, operations, devices and systems may comprise more or fewer steps or components than appear herein, and these steps or components may be combined with one another, in part or in whole.

Furthermore, the present disclosure is not to be limited in terms of the particular embodiments described in this application, which are intended as illustrations of various embodiments. Many modifications and variations can be made without departing from its scope and spirit. Functionally equivalent methods and apparatuses within the scope of the disclosure, in addition to those enumerated herein, will be apparent to those skilled in the art from the foregoing descriptions.

All language such as "up to," "at least," "greater than," "less than," and the like, include the number recited and refer to ranges which can subsequently be broken down into sub-ranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

The terms "computer interface" and "monitor" refer to functional device elements of the present disclosure. A "computer interface" typically includes a central processing unit, memory unit for storing random access memory (RAM) as well as storage memory, input/output connectors and a user-activated sensory device for operation, such as a mouse, keyboard, touch-screen or voice-activated module. A "monitor" can be a visualization device presented on a tablet, phone, other hand-held devices or a stand-alone display. A computer interface and a monitor can be separate or integrated devices. Likewise, a myoelectric controller, a computer interface and a monitor can be separate or integrated devices.

The phrase "orthogonal or other mapping" refers to orthogonal mapping or non-orthogonal mapping. As an example of non-orthogonal mapping, one can map the movement of two or more muscles in directions 45 degrees apart.

What is claimed is:

1. A myoelectric computer interface device comprising:
a myoelectric controller comprising a first myoelectric sensor for generating a first signal from a first muscle when the first muscle is contracted by a subject and a second myoelectric sensor for generating a second signal from a second muscle when the second muscle is contracted by the subject simultaneously with the contraction of the first muscle;
a monitor; and
a computer interface configured to generate a cursor image on the monitor, and to create a vector sum of the first signal and the second signal to move in real time the cursor image along a first axis toward a first target image based upon the first signal from the first myoelectric sensor and to move the cursor image along a second axis toward a second target image based upon the second signal from the second myoelectric sensor, such that a target image can be reached only by the first or second signal being generated in isolation.

2. The myoelectric computer interface device of claim 1, wherein the myoelectric sensors comprise electrodes.

3. The myoelectric computer interface device of claim 2, wherein the electrodes are skin surface electrodes.

4. The myoelectric computer interface device of claim 1, wherein the computer interface is further configured to orthogonally map the second signal relative to the first signal.

5. The myoelectric computer interface device of claim 4, wherein the computer interface is configured to further provide for visualizing a first target position icon and a plurality of additional target position icons as the at least one target image on the monitor.

6. The myoelectric computer interface device of claim 5, wherein the computer interface is configured to further provide for determining at least one distance between the first target position icon and any one of the plurality of additional target position icons.

7. The myoelectric computer interface device of claim 1, wherein the monitor displays movements and locations for a cursor icon, a first target position icon and a plurality of additional target position icons.

8. A method for training uncoupling of co-activated first and second muscles for a subject, comprising
providing a myoelectric computer interface device of claim 1;
performing at least one task with the subject; and
providing real-time feedback to the subject of the activity of the first and second muscles.

9. The method of claim 8, wherein the at least one task comprises of a training task.

10. The method of claim 8, wherein the subject comprises at least one limb; and wherein the myoelectric controller includes at least one sensor configured to attach to a skin surface of the at least one limb of the subject or implant into the at least one limb of the subject.

11. The method of claim 8, wherein the at least one task comprises the subject actuating at least one muscle to effect one of the following actions:
(a) maintenance of the cursor icon at a given position for a time; and
(b) movement of the cursor icon from a first position to a second position.

12. The method of claim 8 wherein the myoelectric computer interface device includes at least one computer-implementable software program comprising executable code for subject-interactive functionality.

13. The method of claim 12, wherein the subject-interactive functionality is selected from skill challenges, progression scales, encouragement mechanisms and inspirational algorithms.

14. The method of claim 12, further comprising performing orthogonal mapping of at least two co-activating muscles for the subject.

15. The myoelectric computer interface device of claim 1 wherein the controller is further configured to measure for each different time the cursor image is moved between an initial position and the first or second target image one or more of a path length traveled by the cursor image between the initial position and the first or second target image and a change in time for the cursor image to travel between the initial position and the first or second target image, to store the measured path length traveled and change in time, to compare the path length traveled and the change in time for each different time the cursor image is moved between an initial position and the first or second target image, and to display the comparison.

16. The myoelectric computer interface device of claim 1 wherein the controller is further configured to cause the first or second target image to change in appearance upon the cursor image being maintained in position over the first or second target image for a predetermined period of time.

17. The myoelectric computer interface device of claim 1 further comprising a third myoelectric sensor for generating a single third signal from a third muscle when the third muscle is contracted by the subject simultaneously with the first muscle, and the computer interface is further configured to create a vector sum of the first signal, second signal and third signal so as to move in real time the cursor image toward the first target image, the second target image, or a third target image, such that a target image can be reached only by the first, second or third signal being generated in isolation.

* * * * *